(12) United States Patent
Williams et al.

(10) Patent No.: US 11,737,908 B2
(45) Date of Patent: Aug. 29, 2023

(54) OSTOMY APPLIANCE

(71) Applicant: Salts Healthcare Limited, Birmingham (GB)

(72) Inventors: Kieran Williams, Birmingham (GB); Lee Tretheway, Birmingham (GB); Iain Powner, Birmingham (GB); Jesus Alfaro, Birmingham (GB); Marcus Allen, Birmingham (GB)

(73) Assignee: Salts Healthcare Limited, Birmingham (GB)

( * ) Notice: Subject to any disclaimer, the term of this patent is extended or adjusted under 35 U.S.C. 154(b) by 259 days.

(21) Appl. No.: 16/649,070

(22) PCT Filed: Sep. 21, 2018

(86) PCT No.: PCT/GB2018/052688
§ 371 (c)(1),
(2) Date: Mar. 19, 2020

(87) PCT Pub. No.: WO2019/058124
PCT Pub. Date: Mar. 28, 2019

(65) Prior Publication Data
US 2020/0261254 A1 Aug. 20, 2020

(30) Foreign Application Priority Data
Sep. 22, 2017 (GB) ...................................... 1715388

(51) Int. Cl.
*A61F 5/448* (2006.01)
*A61F 5/441* (2006.01)
(52) U.S. Cl.
CPC .............. *A61F 5/448* (2013.01); *A61F 5/441* (2013.01)
(58) Field of Classification Search
CPC combination set(s) only.
See application file for complete search history.

(56) References Cited

U.S. PATENT DOCUMENTS

| 4,120,715 A * | 10/1978 | Ockwell | ................. B32B 3/266 |
| | | | 156/289 |
| 4,957,522 A | 9/1990 | Brassell | |

(Continued)

FOREIGN PATENT DOCUMENTS

| EP | 0191646 A2 | 8/1986 |
| EP | 0981311 B1 | 8/2004 |

(Continued)

OTHER PUBLICATIONS

International Search Report and Written Opinion dated Jan. 3, 2019 in corresponding PCT Application No. PCT/GB2018/052688.

(Continued)

*Primary Examiner* — Guy K Townsend
(74) *Attorney, Agent, or Firm* — Leydig, Voit & Mayer, Ltd.

(57) ABSTRACT

An ostomy appliance comprising: first and second walls connected to each other at or near their peripheries, the first wall having a stoma-receiving opening; a connection member connected to the first wall for attaching the appliance to a user; an aperture located in either of the first and/or second walls for permitting waste gases to exit the appliance; a multi-layer filter positioned adjacent and covering the aperture on an exterior surface of the respective first and/or second wall, wherein a layer of the filter is hydrophobic and wherein said hydrophobic layer is positioned directly adjacent the respective first and/or second wall, wherein the hydrophobic layer has a first side and a second side and wherein the first side is connected directly to the respective first and/or second wall, said connection holding the multi-layer filter relative to the wall.

9 Claims, 7 Drawing Sheets

(56) References Cited

U.S. PATENT DOCUMENTS

| | | | |
|---|---|---|---|
| 5,306,264 A | | 4/1994 | Ferguson et al. |
| 6,135,986 A * | | 10/2000 | Leisner ............... A61F 5/441 |
| | | | 604/324 |
| 7,341,578 B2 * | | 3/2008 | Bulow ............... A61F 5/441 |
| | | | 604/338 |
| 8,979,811 B2 * | | 3/2015 | Keleny ............... B01D 46/02 |
| | | | 604/338 |
| 11,529,254 B2 * | | 12/2022 | Tretheway ............ A61F 5/448 |
| 2003/0100870 A1 | | 5/2003 | Villefrance |
| 2005/0070863 A1 * | | 3/2005 | Bulow ............... A61F 5/441 |
| | | | 604/332 |
| 2007/0049880 A1 | | 3/2007 | Suehr et al. |
| 2009/0247970 A1 * | | 10/2009 | Keleny ............ B01D 46/0036 |
| | | | 156/247 |
| 2016/0235581 A1 * | | 8/2016 | Keleny ............... A61F 5/441 |
| 2020/0214872 A1 * | | 7/2020 | Tretheway ............ A61F 5/443 |
| 2020/0214873 A1 * | | 7/2020 | Tretheway ........... A61F 5/4407 |
| 2020/0214875 A1 * | | 7/2020 | Tretheway ............ A61F 5/448 |
| 2020/0276044 A1 * | | 9/2020 | Tretheway ............ A61F 5/441 |
| 2020/0281761 A1 * | | 9/2020 | Tretheway ........... A61F 5/4404 |
| 2020/0289307 A1 * | | 9/2020 | Tretheway ........... A61F 5/4407 |
| 2020/0289308 A1 * | | 9/2020 | Tretheway ............ A61F 5/441 |

FOREIGN PATENT DOCUMENTS

| | | |
|---|---|---|
| EP | 1757252 A2 | 2/2007 |
| EP | 2151219 A1 | 2/2010 |
| GB | 1 596 496 | 8/1981 |
| GB | 2 549 060 | 11/2017 |
| JP | 2002-085439 | 3/2002 |
| WO | WO 98/44880 A1 | 10/1998 |
| WO | WO 2007/030703 | 3/2007 |
| WO | WO-2007030703 A2 * | 3/2007 ............ A61F 5/441 |
| WO | WO 2011150936 A1 | 12/2011 |

OTHER PUBLICATIONS

Search Report dated Feb. 27, 2019 in corresponding GB Application No. GB 1815384.1.
Search Report dated Sep. 29, 2021 in corresponding Great Britain Patent Application GB2112714.7.
Examination Report dated Mar. 1, 2022 in corresponding Great Britain Patent Application GB2112714.7.
Search Report dated Sep. 29, 2021 in corresponding Great Britain Patent Application GB2112715.4.
Examination Report dated Feb. 28, 2022 in corresponding Great Britain Patent Application GB2112715.4.
Search Report dated Sep. 29, 2021 in corresponding Great Britain Patent Application GB2112717.0.
Extended European Search Report dated May 16, 2022 in corresponding European Patent Application No. 22154104.8.
Extended European Search Report dated May 16, 2022 in corresponding European Patent Application No. 22154106.3.
Extended European Search Report dated May 16, 2022 in corresponding European Patent Application No. 22154108.9.
European Office Action dated May 16, 2023 in corresponding European Patent Application No. 18778988.8.
Australian Office Action dated Jun. 22, 2023 in corresponding Australian Patent Application No. 2018336051.

* cited by examiner

OSTOMY APPLIANCE

CROSS-REFERENCE TO RELATED APPLICATIONS

This application is a U.S. National Stage Application filed under 35 U.S.C. § 371 of International Application No. PCT/GB2018/052688, filed Sep. 21, 2018, which claims the benefit of Great Britain Application No. 1715388.3, filed Sep. 22, 2017. Both of these applications are hereby incorporated by reference in their entireties.

DESCRIPTION OF INVENTION

The invention relates to an ostomy appliance for collecting human waste. It should be understood that the invention can be utilised in drainable and non-drainable ostomy appliances.

It is known to provide in a wall of an ostomy appliance ('bag' or 'pouch' as they are commonly known in the art) an aperture to permit waste gases to escape from a waste collecting chamber of the ostomy appliance. This is necessary to prevent the bag expanding too much with gas and potentially from leaking or bursting whilst filled with waste. In some prior art ostomy appliances the aperture is covered by a filter, the purpose of which is to de-odorise the waste gases before they exit to atmosphere. In the known ostomy appliances the aperture and filter are usually positioned in an upper part of the bag above a stoma receiving opening. Such filters are usually, but not always, positioned inside the exterior wall of ostomy appliance so that waste gas must pass through the filter before exiting the bag via the aperture.

Although intermediate walls are often provided in between the exterior walls in order to create a tortuous path for waste gas to travel through in order to get to the filter, thus making it difficult for bodily waste to come into contact with the filter, these walls are quite often unsuccessful in keeping bodily waste away from the filter. In this case, the filter can become blocked during use which causes the appliance to gradually inflate with waste gases with no means of escaping, causing discomfort and/or embarrassment to the user.

The present invention looks to address this problem.

According to a first aspect of the invention, we provide an ostomy appliance comprising:—
first and second walls connected to each other at or near their peripheries, the first wall having a stoma-receiving opening;
a connection member connected to the first wall for attaching the appliance to a user;
an aperture located in either of the first and/or second walls for permitting waste gases to exit the appliance;
a multi-layer filter positioned adjacent and covering the aperture on an exterior surface of the respective first and/or second wall,
wherein a layer of the filter is hydrophobic and wherein said hydrophobic layer is positioned directly adjacent the respective first and/or second wall,
wherein the hydrophobic layer has a first side and a second side and wherein the first side is connected directly to the respective first and/or second wall, said connection holding the multi-layer filter relative to the wall.

Embodiments of the invention will now be described by way of example only with reference to the accompanying drawings, of which:—

Figure 1:
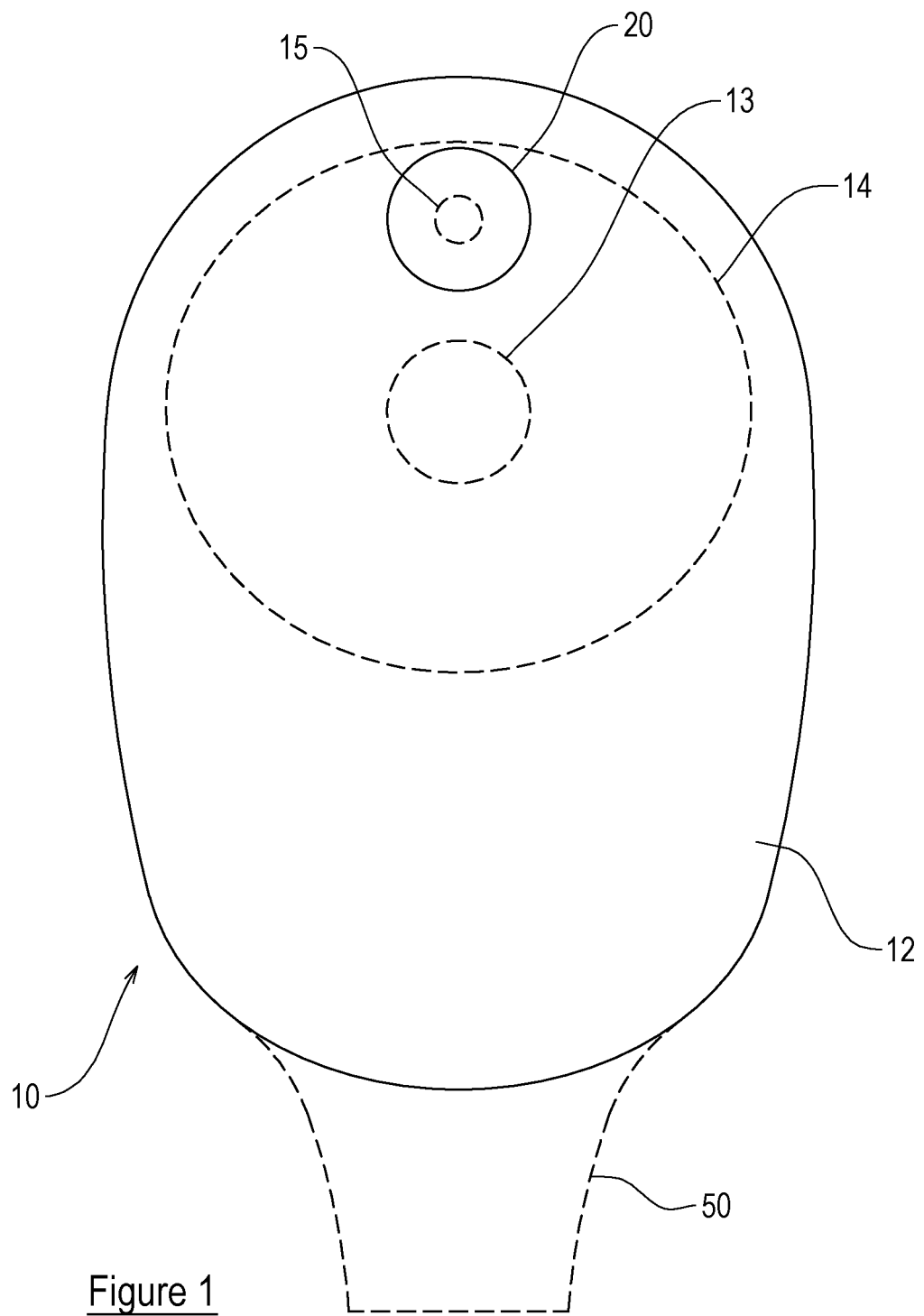
FIG. 1 is a front view of a first embodiment of an ostomy appliance in accordance with the present invention.
Figure 2:
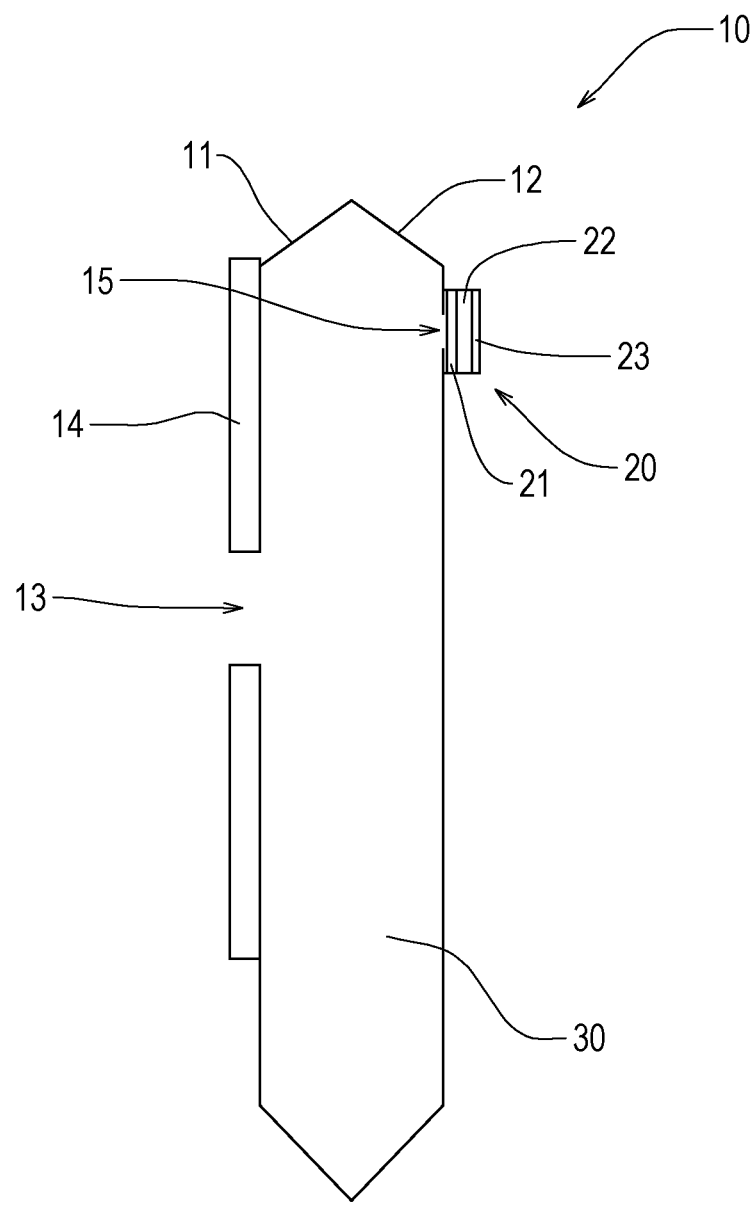
FIG. 2 is a side cross-sectional view of the ostomy appliance of FIG. 1.
Figure 3:
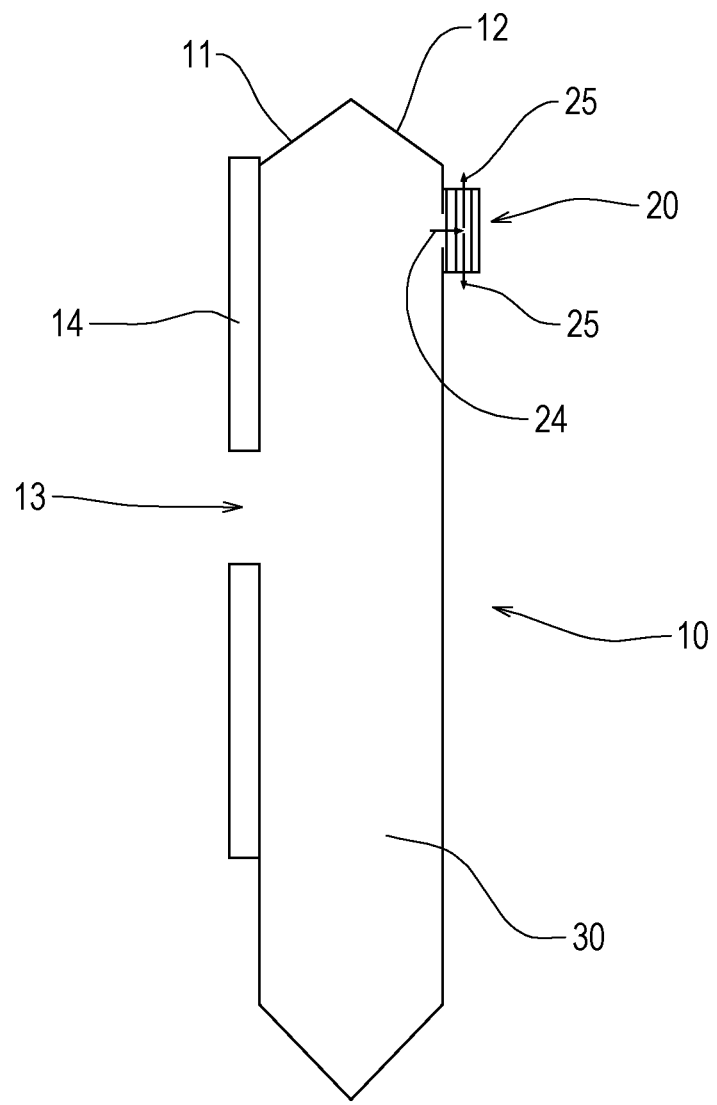
FIG. 3 is a further side cross-sectional view of the ostomy appliance of FIG. 1.

Referring firstly to FIGS. 1 to 3 these show a first embodiment of an ostomy appliance in accordance with the present invention, shown generally at 10. The general construction of the ostomy appliance 10 is similar to those well known in the art and in that sense it includes first 11 and second 12 walls which are connected to each other at or near their peripheries, for example by welding or using an adhesive. The ostomy appliance 10 shown could be a drainable appliance, meaning that its contents could be emptied through an outlet (50, shown in broken lines) between the first 11 and second 12 walls.

The first wall 11 has a stoma-receiving opening 13 and is connected to a generally circular connection member 14 in the form of a flange for adhering the appliance 10 to a user around their stoma. The connection member 14 could be any appropriate shape, however.

The ostomy appliance 10 defines at least one chamber therein. A waste collecting chamber 30 is provided which communicates with the stoma-receiving opening 13 and, if the ostomy appliance is a drainable appliance, at its lower end with an outlet (50). The waste collecting chamber 30 is defined between the first 11 and second 12 walls and is provided as the primary chamber for collecting a user's waste, which enters the chamber through the opening 13 in the first wall 11. More chambers (not shown) may be provided within the ostomy appliance, for example in order to create a tortuous path for the waste gas to exit the appliance and/or to allow fluid in a further chamber to pass into the waste collecting chamber 30 via a non-return valve.

An aperture 15 is provided in the second wall 12 to permit waste gas within the ostomy appliance 10 to exit the appliance. The aperture 15 is preferably in use provided above the stoma-receiving opening 13 to reduce the likelihood of waste collected in the waste collecting chamber 30 from getting near to the aperture 15. The aperture 15 is preferably circular in shape but can be formed in a number of different shapes. The aperture 15 could in some embodiments of the present invention include a plurality of apertures in the form of perforations provided in the second wall 12. Although the aperture 15 is shown in FIG. 1 as being provided in the second wall 12, it may instead be provided in the first wall 11. Alternatively, apertures may be provided on both the first 11 and second 12 walls.

A filter 20 is provided externally of the ostomy appliance 10 as shown in FIGS. 1 and 2. More specifically the filter 20 is attached to an exterior surface of the second wall 12. The filter 20 is attached to the second wall 12 adjacent the aperture 15 so that the aperture is fully covered by the filter 20. It can be seen on FIG. 1 that the aperture 15 is a smaller diameter than the diameter of the filter 20. Therefore, any waste gases that exit the ostomy appliance 10 through the aperture 15 must pass through the filter 20 in order to pass to atmosphere. The filter 20 is attached by an adhesive connection, although it could be connected in any appropriate way, for example heat welding.

Figure 7:
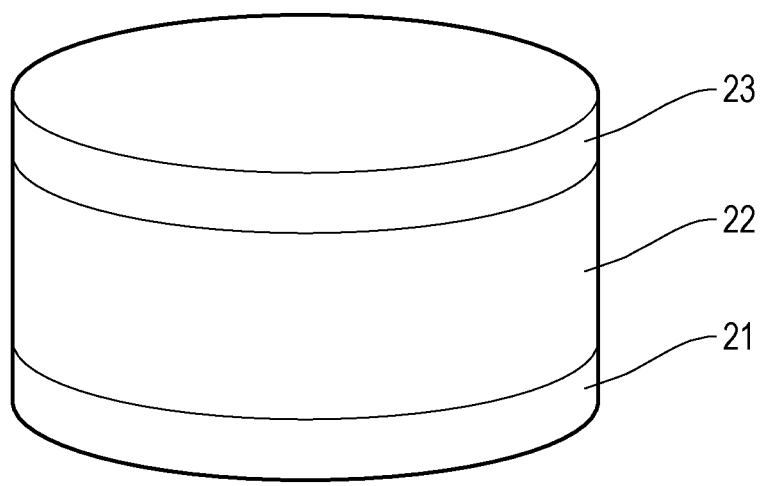
FIG. 7 is a perspective view of an example of a multi-layer filter for use in the first and second embodiments of ostomy appliance.

The filter 20 is a multi-layered filter as shown in more detail in FIG. 7. The multi-layered filter 20 preferably consists of three layers (although it could have more layers), including a hydrophobic layer 21, a de-odorising layer 22 and a gas and liquid impermeable layer 23. The multi-layered filter 20 is preferably constructed (but not limited to) in the order of hydrophobic layer 21, de-odorising layer 22 and gas and liquid impermeable layer 23.

The hydrophobic layer 21 is preferably Polytetrafluoroethylene (PTFE). The hydrophobic nature of PTFE ensures that water molecules are repelled from its surface, meaning that any interaction between the surface of the PTFE layer and water molecules is substantially resisted, and thus, the PTFE layer is waterproof. The hydrophobic layer 21 of the multi-layered filter 20 is advantageously positioned directly adjacent the second wall 12 so as to directly and completely cover the aperture 15 provided in the second wall 12. The hydrophobic layer 21 has a first side and second side with the first side connected directly to the second wall 12, said connection holding the multi-layer filter relative to the wall 12. The hydrophobic layer 21 is connected directly to the second wall 12 preferably by an adhesive, e.g. a holt melt adhesive or double-sided tape. Therefore, the hydrophobic layer 21 is in direct fluid communication with the waste collecting chamber 30 such that any waste gas exiting the ostomy appliance 10 must travel through the hydrophobic layer 21 first. The advantage of providing the hydrophobic layer 21 directly adjacent the aperture 15, and thus facing inwards towards the interior of the appliance 10, is that no liquid waste collected in the waste collecting chamber 30 can pass through the hydrophobic layer 21 and into contact with the other layers of the multi-layered filter 20. This reduces the risk of the filter, in particular the de-odorising layer 22, from getting damp and/or clogged. A damp and/or clogged filter can lead to ballooning of the ostomy appliance which can significantly reduce the effectiveness of the filter and the appliance. This will inevitably lead to the user having to replace the flawed ostomy appliance at a cost to the user.

Further to this, the multi-layered filter 20 is advantageously positioned on an external surface of the second wall 12 such that the de-odorising layer 22 and gas and liquid impermeable layer 23 cannot come into direct contact with the waste collected in the waste collecting chamber 30 which significantly reduces the risk of the filter 20 from getting damp and/or clogged. Further to this, providing a filter 20 externally of the ostomy appliance 10, e.g. external of the wall or walls which form the waste collecting chamber, allows for an easier and thus more cost effective manufacturing process as there is no need to place the filter carefully between layers of the ostomy appliance before they are connected together. Instead, the filter 20 can, if desired, be attached to the ostomy appliance once the walls of the appliance have been sealed together around its peripheries.

The de-odorising layer 22 is preferably a layer of carbon based de-odorising material that is positioned directly adjacent the hydrophobic layer 21 such that it lies on an opposite side of the hydrophobic layer 21 to the aperture 15 and wall 12. The de-odorising layer 22 receives waste gas travelling from the hydrophobic layer 21 and de-odorises the waste gas such that it is ready to exit the de-odorising layer 22 into atmosphere.

The gas and liquid impermeable layer 23 is preferably a layer of Cryovac™ material that does not allow gas or liquid to pass through its surface. The gas and liquid impermeable layer 23 is positioned directly adjacent the de-odorising layer 22 such that it lies on an opposite side of the de-odorising layer 22 to the hydrophobic layer 21. The gas and liquid impermeable layer 23 advantageously partially protects the de-odorising layer 22 from getting damp and/or clogged by moisture that is provided externally of the ostomy appliance, for example when a user is showering.

Referring to FIG. 3, arrows 24, 25 show the directional flow path taken by waste gas when exiting the waste collecting chamber 30 through the filter 20. Firstly, the waste gas travels through the aperture 15 and into the hydrophobic layer 21 in a direction substantially perpendicular to the second wall 12.

Thereafter the waste gas continues to travel through the hydrophobic layer 21 and into the de-odorising layer 22 in a direction substantially perpendicular to the second wall 12. Finally, the waste gas travels through and exits the de-odorising layer 22 in a direction substantially parallel to the second wall 12, i.e. radially away from an axis of the filter 20. The positioning of the gas and liquid permeable layer 23 directly adjacent the de-odorising layer 21 ensures that all gas entering the filter passes through the de-odorising layer in a direction substantially parallel to the second wall 12.

Figure 4:
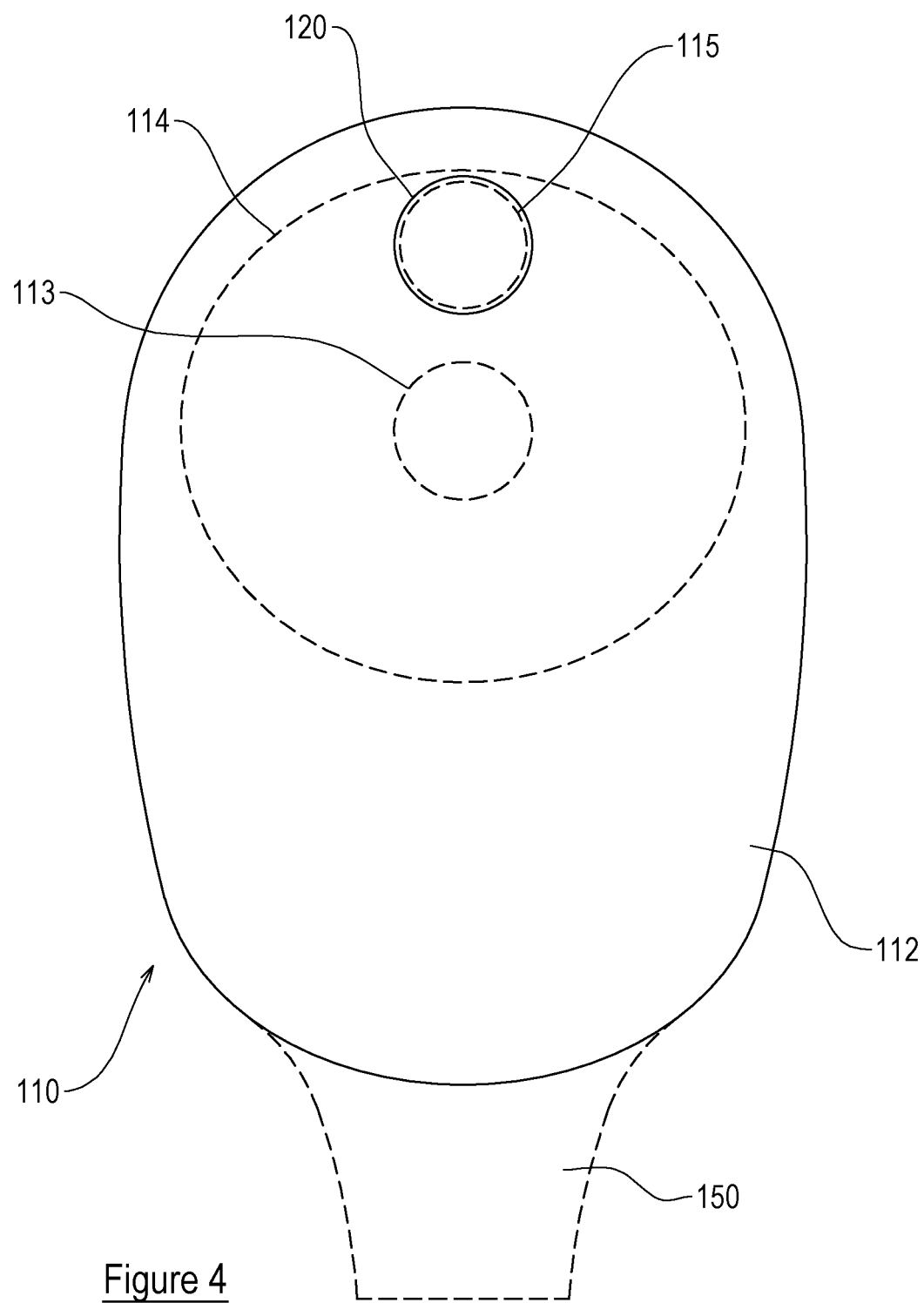
FIG. 4 is a front view of a second embodiment of an ostomy appliance in accordance with the present invention.
Figure 5:
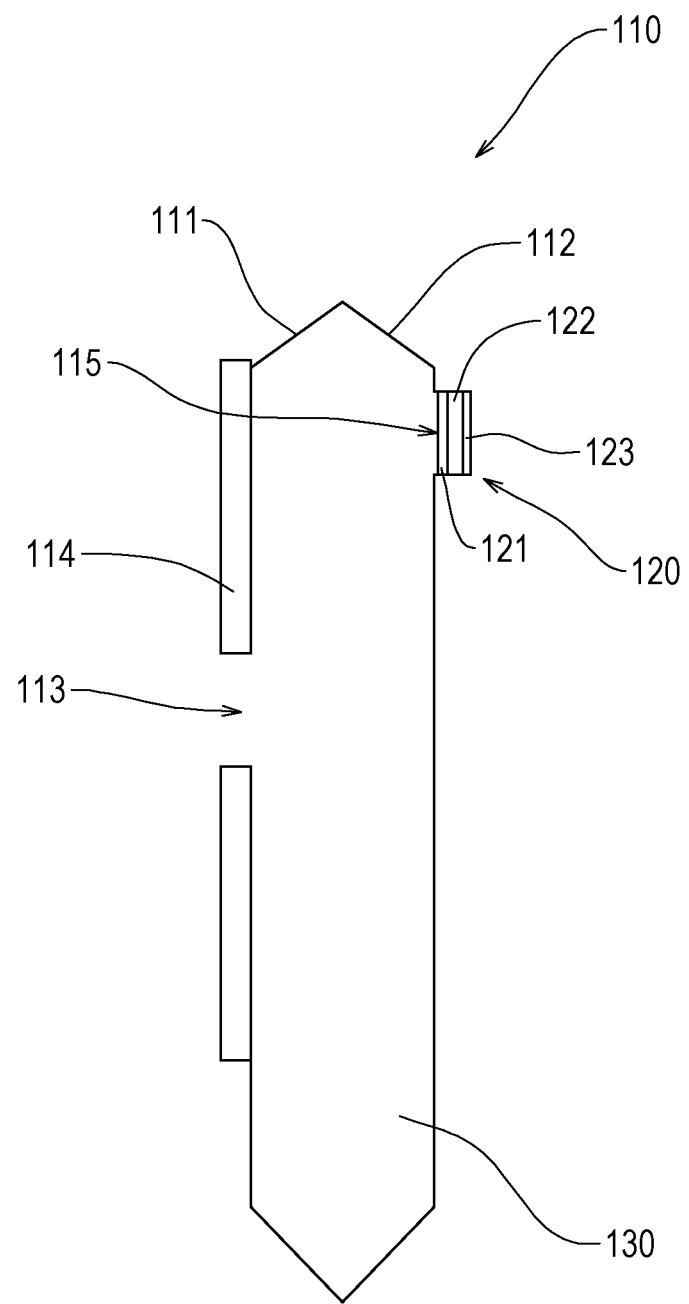
FIG. 5 is a side cross-sectional view of the ostomy appliance of FIG. 4.
Figure 6:
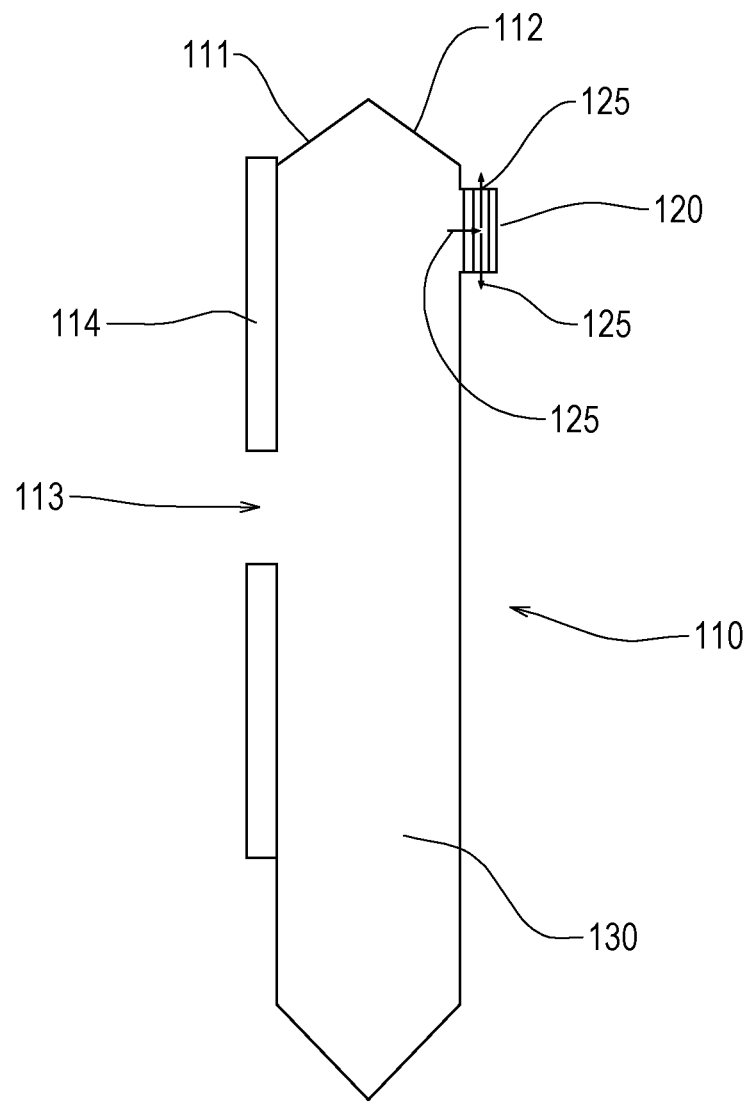
FIG. 6 is a further side cross-sectional view of the ostomy appliance of FIG. 4.

FIGS. 4 to 6 show a second embodiment of an ostomy appliance 110. Features which are in common with the first embodiment 10 have been given the same reference numeral with the addition of 100. Those features will not be discussed again here.

Referring to the second embodiment the main difference is the size of the aperture 115 in relation to the multi-layered filter 120. Instead of the aperture 115 being significantly smaller in diameter than the filter 120, the aperture 115 is substantially the same diameter as the filter 120. This provides for an increased area through which the waste gas can exit the ostomy appliance through the aperture 115 and into and through the hydrophobic layer 121 and further reduces the risk of the aperture 115 becoming completely blocked with waste. The flow through the aperture 115 and multi-layered filter 120 is substantially the same as that of the first embodiment, as shown by arrows 124, 125.

Whilst in the described embodiments the filter is shown as circular in front view, it should be appreciated that other shapes of filter could be used without departing from the scope of the present invention. In addition, whilst the filter described above has three layers, it should be appreciated that a two layer filter could be used, but also filters of four or more layers could be used.

When used in this specification and claims, the terms "comprises" and "comprising" and variations thereof mean that the specified features, steps or integers are included. The terms are not to be interpreted to exclude the presence of other features, steps or components.

The features disclosed in the foregoing description, or the following claims, or the accompanying drawings, expressed in their specific forms or in terms of a means for performing the disclosed function, or a method or process for attaining the disclosed result, as appropriate, may, separately, or in any combination of such features, be utilised for realising the invention in diverse forms thereof.

The invention claimed is:

1. An ostomy appliance comprising:
   first and second walls connected to each other at or near their peripheries, the first wall having a stoma-receiving opening;
   a connection member connected to the first wall for attaching the appliance to a user;

an aperture located in either of the first and/or second walls for permitting waste gases to exit the appliance;

a multi-layer filter positioned adjacent and covering the aperture on an exterior surface of the respective first and/or second wall, wherein a layer of the filter is hydrophobic and wherein said hydrophobic layer is positioned directly adjacent the respective first and/or second wall, wherein the hydrophobic layer has a first side and a second side and wherein an interior surface of the first side is connected directly to the exterior surface of the respective first and/or second wall, said connection between the interior surface of the first side of the hydrophobic layer and the exterior surface of the respective first and/or second wall being able to hold the multi-layer filter relative to the wall, wherein the filter includes a de-odorising layer positioned adjacent the hydrophobic layer;

wherein the filter includes a gas and liquid impermeable layer positioned adjacent the de-odorising layer;

wherein waste gas travels through the de-odorising layer in a direction substantially parallel to the respective first or second wall; and wherein the gas and liquid impermeable layer is configured to ensure that, in use, all gas entering the filter passes through the de-odorising layer in a direction substantially parallel to the respective first or second wall.

2. The appliance according to claim 1 wherein the hydrophobic layer is Polytetrafluoroethylene (PTFE).

3. The appliance according to claim 1 wherein the interior surface of the first side of the hydrophobic layer is connected directly to the exterior surface of the respective first and/or second wall by an adhesive.

4. The appliance according to claim 1 wherein the de-odorising layer is preferably carbon based.

5. The appliance according to claim 1 wherein the layers of the filter are arranged in the order of hydrophobic layer, de-odorising layer and gas and liquid impermeable layer.

6. The appliance according to claim 5 wherein the de-odorising layer is positioned directly adjacent the hydrophobic layer and wherein the gas and liquid impermeable layer is positioned directly adjacent the de-odorising layer.

7. The appliance according to claim 1 wherein waste gas travels through the aperture in a direction substantially perpendicular to the first and/or second wall.

8. The appliance according to claim 1 wherein waste gas travels through the hydrophobic layer in a direction substantially perpendicular to the first and/or second wall.

9. The appliance according to claim 3 wherein the adhesive is a hot melt adhesive or double sided tape.

* * * * *